April 18, 1961 W. A. ROBBINS Plant Pat. 2,050
MUSHROOM PLANT
Filed Feb. 5, 1959
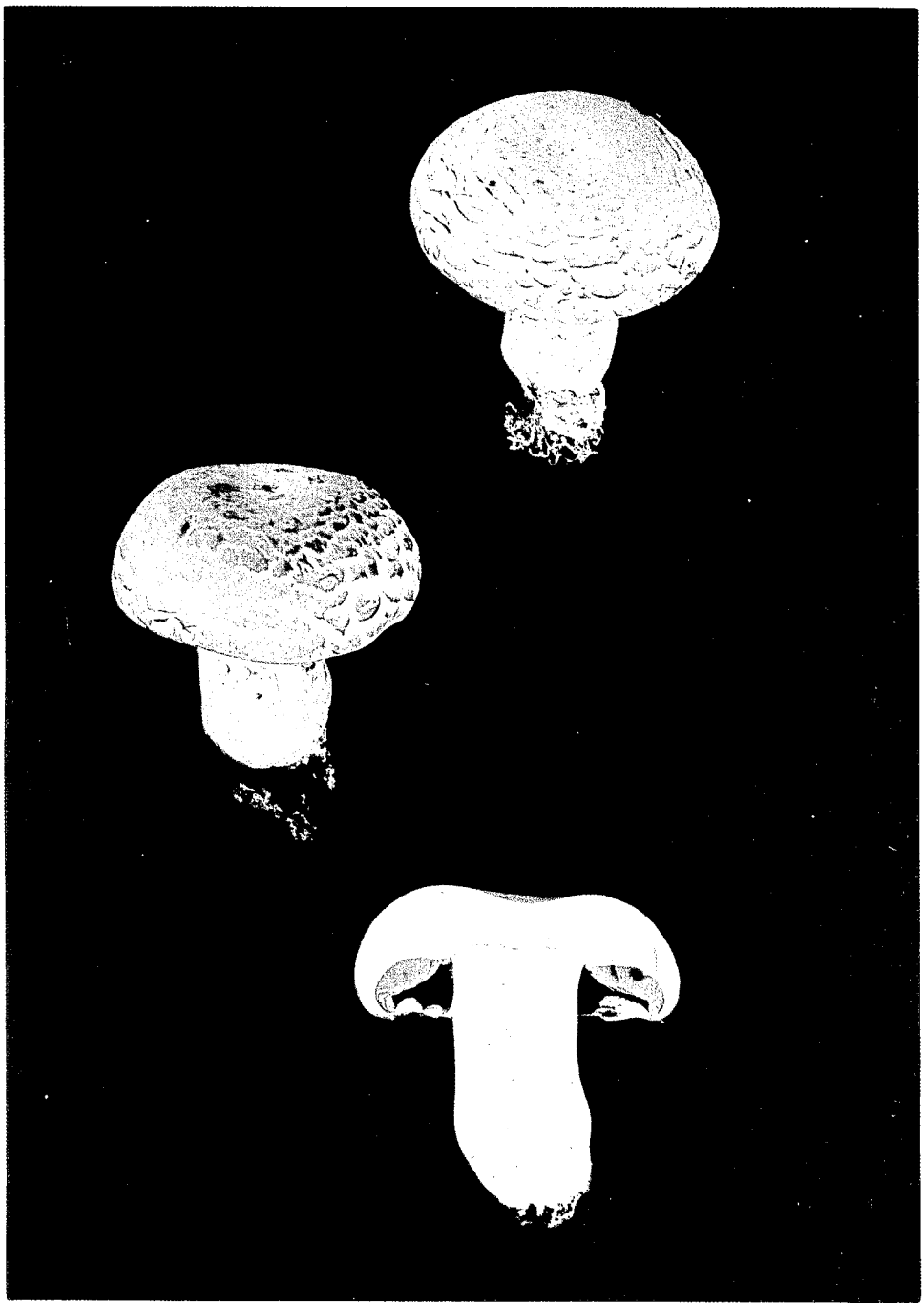
Inventor:
Wayne A. Robbins
by Howson & Howson Attys.

United States Patent Office

Plant Pat. 2,050
Patented Apr. 18, 1961

2,050

MUSHROOM PLANT

Wayne A. Robbins, St. Charles, Ill., assignor to Campbell Soup Company, Camden, N.J., a corporation of New Jersey Filed Feb. 5, 1959, Ser. No. 791,508

1 Claim. (Cl. 47—59)

The present invention relates to a new and distinct horticultural variety of mushroom plant of *Agaricus bisporus* (Lange) Singer, variety *avellanea*.

This new variety of mushroom plant was discovered as a sector in a pure culture grown on nutrient agar in a laboratory in West Chicago, Du Page County, Illinois, where culture studies were being made and was grown in a cultivated mushroom bed in West Chicago, Du Page County, Illinois; and has been asexually reproduced many times by the applicant by propagating mycelial transfers at West Chicago, Du Page County, Illinois. Also, this mushroom plant has been reproduced by means of germinating spores at West Chicago, Du Page County, Illinois.

The outstanding characteristics of this mushroom plant are its increased yield in pounds per square foot of mushroom bed as compared with the yield of standard mushroom plants including both the white variety, *Agaricus bisporus* (Lange) Singer, variety *albida*, and the cream variety, *Agaricus bisporus* (Lange) Singer, variety *avellanea*; by its larger size and greater productivity than the standard mushroom plants; and by the fact that the mycelium grown in compost is finer and grayer and more prolific in pinning on the bed. Further, when compared to the typical white and cream mushroom plants widely grown commercially the caps and stems of this mushroom plant are thicker and have greater density and the cooked mushroom plant is firmer in consistency and stronger in flavor than the typical white and cream mushroom plants.

This mushroom plant is of a type called "cream" in the trade. The cap is scaly and colored, the color being concentrated in the scales and increasing in intensity with increasing scaliness. Normally, this mushroom plant is colored a light yellowish pink and is moderately scaled; however, under drought conditions or relatively high air movement the caps are quite scaly and colored a brownish orange. At maturity the cap frequently is strongly depressed in the center.

The accompanying drawings illustrate several forms of the mushroom plants of the present invention, the darker mushroom plant being grown under drought conditions, the lighter one being grown under more moist conditions.

The following detailed description of the mushroom plant of the present invention is given with reference to the Nickerson Color Fan (Maximum Chroma-Forty Hues) 1957. This description is of a mushroom plant grown under commercial conditions and in commercial mushroom plant producing structures. When this mushroom plant is grown under different conditions, it will be obvious that its appearance may be different than that described.

The cap or pileus of the mushroom plant, when the veil breaks, varies between approximately 2 to 12 centimeters in diameter and is of generally convex shape with a depression in the top center which is quite pronounced during the first flush and decreases with later flushes until the center reaches a generally plane relation. The epicutis consists of oppressed elongated hyphae. The cap is squamose with the scales being patchlike and they range from 0.2 to 0.6 centimeter in width. The scales are colored from a light yellowish pink near 2.5YR 9.3/2.5 to a brownish orange near 2.5YR 5/5. When the mushroom plant is grown under drought or relatively high air movement conditions, the usual color is similar to 2.5YR 8/4 and is concentrated in the scales. The color on the inflex border of the pileus is 2.5YR 8/3. The trama is white, unchanging in wounds, but becoming slightly reddish in age. The margin is incurved and exceeds the gills.

The hymenophores are lamellate with the lamellae being free and unequal. The lamellae are generally equal to color 2.5YR 8.5/4 when immature and change to 2.5YR 4 3/6 when the partial veil breaks and change further to a slightly darker shade when the spore matures. The basidia are of small size and are consistently two-spored.

The stipe, without a cellular covering, is striate and vary between 1.5 to 7 centimeters long and from 0.8 to 3.5 centimeters in diameter with a bulbous base. The stipe is white below the annulus and its color above the annulus, without a volva, is 2.5YR 9/3.

The annulus is formed by separation of the partial veil which takes place between the stipe and the margin of the cap. The annulus is on the upper one-third of the stipe when the veil breaks and is thick and almost fleshy. Its color adjacent to the stipe is 2.5YR 8/3 and the color fades gradually toward the margin of the annulus. The edge of the annulus is lacerated when the veil breaks.

The hyphae are septate and multinucleate and have no clamp connections.

The spores are generally elliptical or oval and vary from 4 to 6 by 6 to 8 microns.

The spore print color is the equivalent of 7YR 3.8/3.

I claim:

A new and distinct variety of mushroom plant substantially as shown and described characterized particularly as to novelty by its greater productivity and firmer consistency and stronger flavor when cooked, and by the color of the scales, varying from a light yellowish-pink when grown under moist conditions to a brownish-orange when grown under drought or relatively high air movement conditions.

No references cited.